US006896685B1

(12) United States Patent
Davenport

(10) Patent No.: US 6,896,685 B1
(45) Date of Patent: May 24, 2005

(54) SUTURE DEVICE

(76) Inventor: James A. Davenport, 15275 Cadillac Dr., San Antonio, TX (US) 78240

( * ) Notice: Subject to any disclaimer, the term of this patent is extended or adjusted under 35 U.S.C. 154(b) by 113 days.

(21) Appl. No.: 10/353,732

(22) Filed: Jan. 29, 2003

(51) Int. Cl.[7] .............................................. A61B 17/04
(52) U.S. Cl. ...................................... 606/144; 606/139
(58) Field of Search ............................... 606/139, 144, 606/213

(56) References Cited

U.S. PATENT DOCUMENTS

| | | | | |
|---|---|---|---|---|
| 5,320,632 A | * | 6/1994 | Heidmueller | ................ 606/144 |
| 5,364,408 A | | 11/1994 | Gordon | |
| 5,403,328 A | * | 4/1995 | Shallman | ..................... 606/144 |
| 5,403,329 A | | 4/1995 | Hinchecliffe | |
| 5,462,561 A | * | 10/1995 | Voda | ........................... 606/144 |
| 5,527,321 A | * | 6/1996 | Hinchliffe | .................... 606/144 |
| 5,578,044 A | | 11/1996 | Gordon et al. | |
| 5,586,986 A | | 12/1996 | Hinchliffe | |
| 5,626,588 A | | 5/1997 | Sauer et al. | |
| 5,817,108 A | * | 10/1998 | Poncet | ........................ 606/139 |
| 5,964,773 A | | 10/1999 | Greenstein | |

* cited by examiner

Primary Examiner—Gary Jackson
(74) Attorney, Agent, or Firm—Daniel D. Chapman; Jackson Walker L.L.P.

(57) ABSTRACT

The present invention is a suture device generally intended for use in puncture wounds of a body cavity. The suture device can be inserted through the tissue layer into the body cavity and extend needles attached to a common suture line, under endoscopic vision, for engagement with the internal side of the tissue layer. The needles are deployed using a straight spring that deforms outwardly from the shaft of the suture device when a force is applied to the spring. Because of the inherent characteristics of the spring, it bends perpendicular to the shaft of the suture device and the removably attached needle is moved outwardly while staying generally parallel to the shaft of the suture device. Once the force is removed on the spring, the spring returns to its original position close to the body of the shaft.

35 Claims, 3 Drawing Sheets

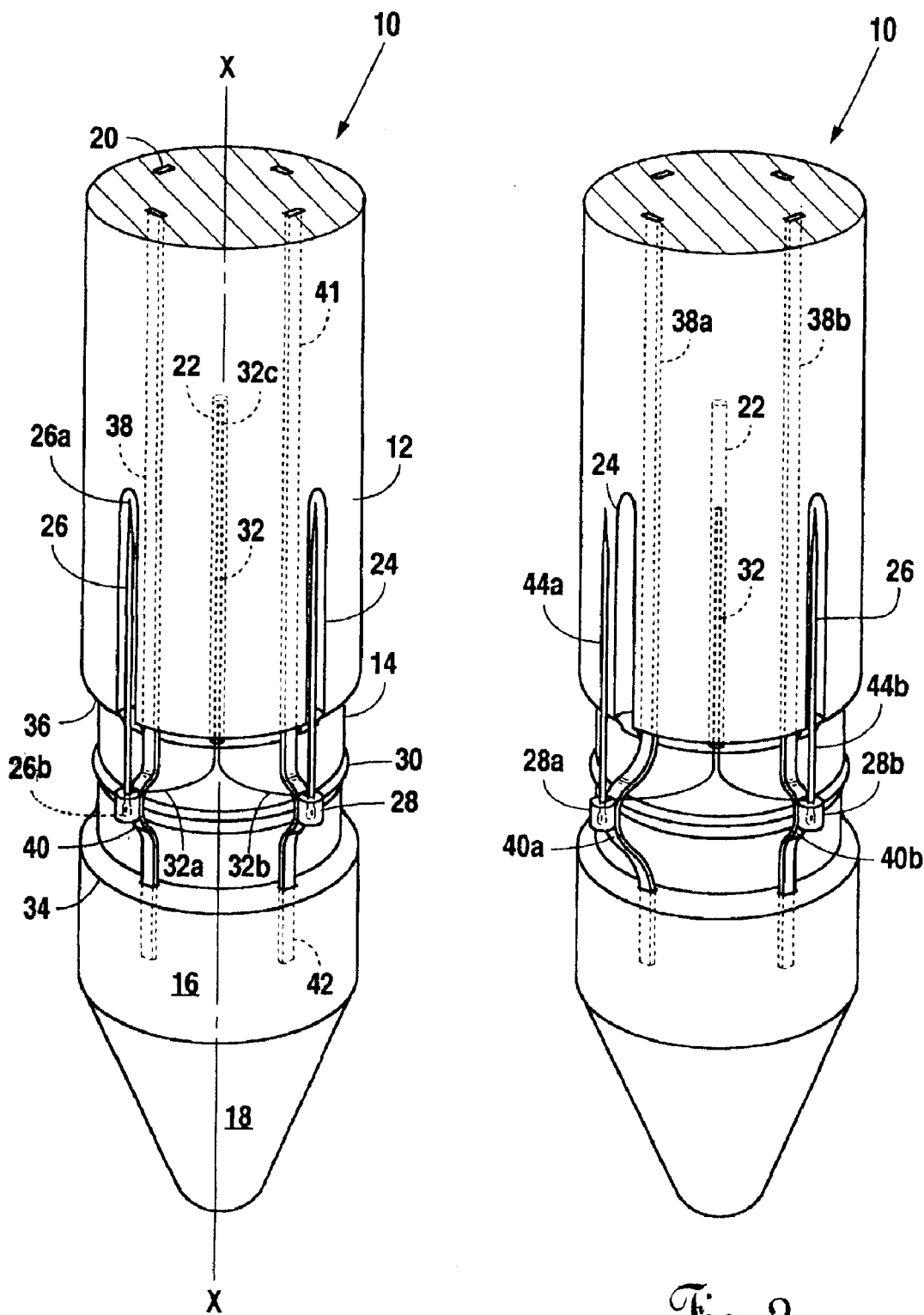

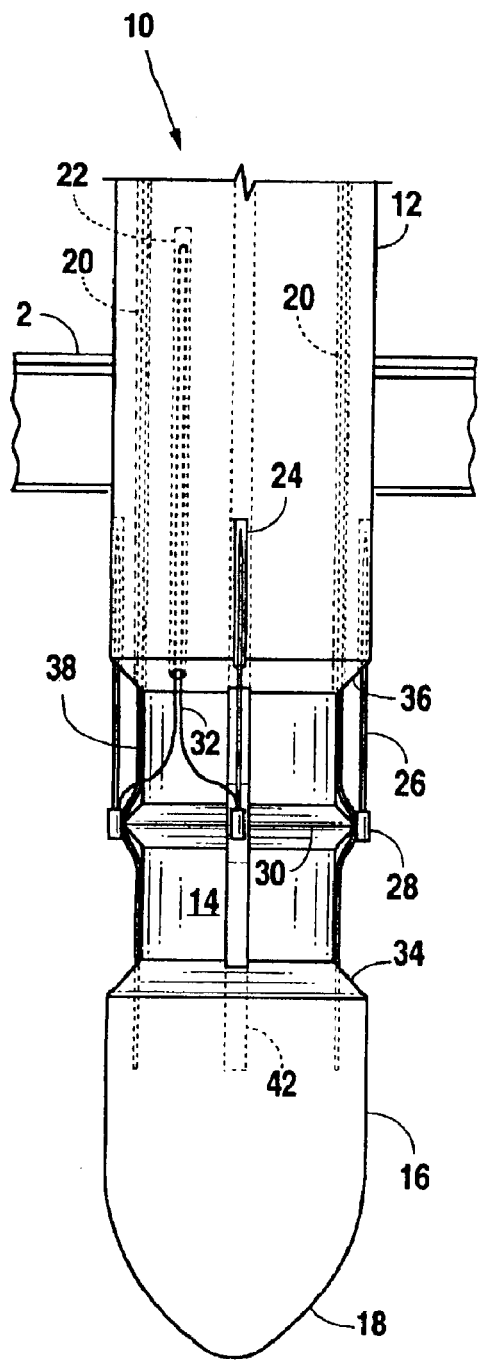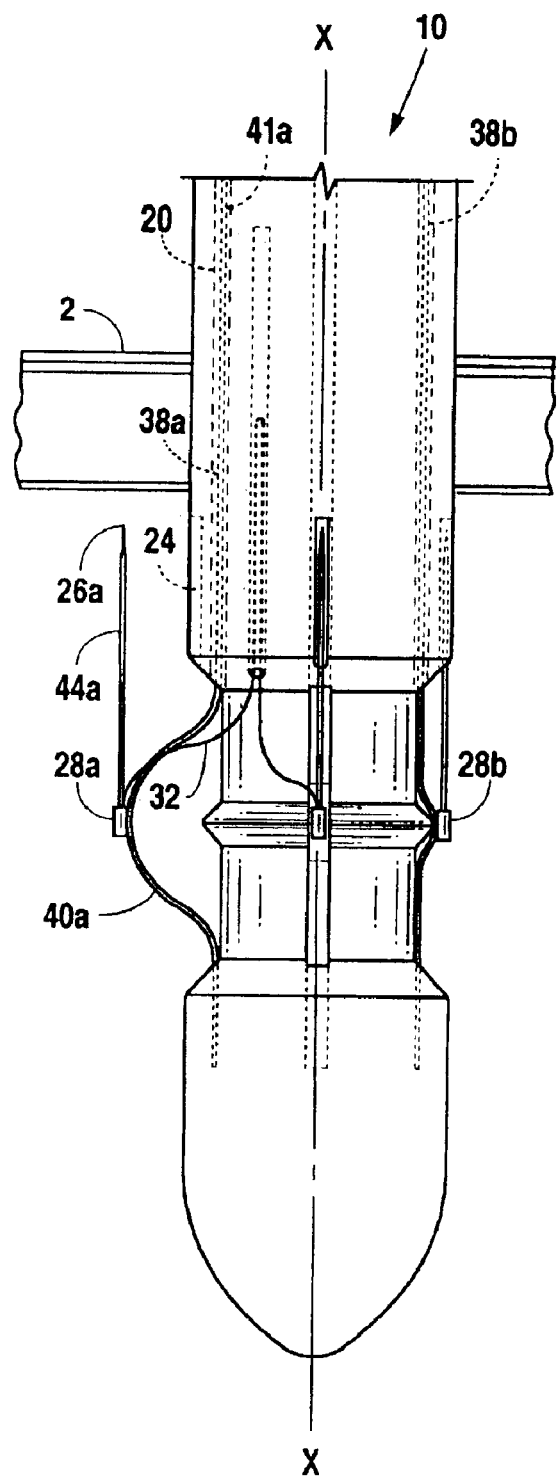
Fig. 3A
Fig. 3B

SUTURE DEVICE

BACKGROUND OF THE INVENTION

1. Field of the Invention

Applicant's invention relates to a device for suturing together the tissue walls of body cavities that have received puncture type wounds. More particularly, it relates to a suture device that can be inserted into the body cavity through the puncture wound, extend needles connected by a suture line and draw them through the tissue walls in order to close the puncture wound.

2. Background Information

Conventional instruments for closing puncture wounds generally provide for a device with a shaft that can be extended into the body cavity through the puncture wound, and then deploy needles for pulling up through the tissue walls. However, the means for deploying the needles are often cumbersome, or the needles are deployed at an angle that is not parallel to the shaft of the suture device. These characteristics mean that either it may be difficult to extend or retract the needle, or the needle may not be pulled perpendicularly through the tissue layer.

The need for a device that allows the needle to be engaged with the tissue layer from inside of the body cavity arises in the case of puncture wounds. These wounds may be accidental, as in the case of trauma, or intentional, as in the case of a surgical procedure. Although not exclusive, one of the most common occasions that calls for this type of device is during an endoscopic surgical procedure. As a general statement regarding these procedures, an incision is made creating an opening for access by the surgeon to the patient's abdominal or chest cavities. In some surgical procedures, a trocar and cannula may be used so that the access opening is created, but the body cavity remains relatively airtight and gas can be pumped into the body cavity expanding the body wall and making organs more accessible. In these situations, it is desirable to suture close the incisions starting from the inside of the body. To this end, several devices have been developed.

The general criteria for these devices is the need for a shaft that may be extended through the incision into the body cavity with the needles and suture line attached to the insertion end of the shaft. Additionally, in order to be able to smoothly insert the shaft and needles, the needles must be shielded from catching on the body tissue as the shaft is inserted through the incision. This necessitates that such devices incorporate mechanisms to extend and retract the needles from the shaft. Conventional devices use various means to deploy the needles. For example, there are instances where the needles are curved and are extended from a pivot point at the base of the needle. Other inventions incorporate various types of gearing and sliding members to effect the deployment of the needles. Unfortunately, conventional deployment mechanisms can be cumbersome and not as efficient as necessary in surgical procedures that require precision. Additionally, surgeons want to be able to accurately insert the needle in the tissue layer and have the needle pierce the insertion point and the fascia layer parallel to the wound or incision edge. This requires that the needle be positioned along a known axis and the most intuitive is parallel to the shaft of the instrument.

Thus, there is a need for a device for suturing closed puncture wounds and body cavities that will quickly and precisely extend and retract a needle and suture, and, while doing so, keep the needle parallel to the shaft of the instrument.

SUMMARY OF THE INVENTION

The present invention is a suturing device that quickly and easily extends and retracts suturing needles from the shaft.

The present invention also provides a means by which the needles are kept generally parallel to the shaft of the instrument.

The present invention further provides:

a. a shaft for inserting the needles and suture into the puncture wound;

b. needle recesses into which the needles can be retracted in order to more easily pass the shaft tip into and through the body wall;

c. a chamber for holding excess suture line;

d. a spring that bends at a predetermined point when force is applied at the end having elastic characteristics;

e. an activator to apply force to the spring;

f. a crimp member may be included to help cause deformation of the spring at a predetermined point; and g. the diameter of the shaft may be sized to fit through a cannula.

In order to solve the difficulties presented in attempting to obtain these features, a suture device has been developed which incorporates a spring as a means for extending the needle from the needle recess outwardly from the shaft.

Specifically, the present invention provides for a spring with elastic characteristics that will deform and bend outwardly from the shaft when pressure is applied to the spring upper portion. Because of the characteristics of the spring and the design of the present invention, the spring deforms at a predetermined point along its length. The needle and suture are attached to the spring by means of a needle receiver. The elastic properties of the spring cause it to deform and move outwardly from the shaft to a second tensioned position when force is applied to the spring upper portion in a direction along the length of the spring. Those same elastic characteristics cause the spring to return to its first relaxed position, and to remain at that first position, when the force is removed from the spring upper portion. Because the needle receiver is attached to the spring crimped portion at the point where the apex of the bend in the spring occurs, the tensioning of the spring causes the extension of the needle receiver, along with the needle, from the first position to the second position. Relaxing the spring moves the needle receiver back to the first position, and if the needle was not deployed, it withdraws the needle back into the needle recess as well.

In order to efficiently use the present invention's deployment means, the needle receiver should be attached to the spring at or near the point where the apex of the bend in the spring occurs when it is in the second position. Additionally, the bend should occur at or near the same point along the spring each time the spring is urged to the second position. In order to accomplish this, several varying means may be employed. A consistent point of bend, or apex, is encouraged by the manner of the engagement of the spring to the shaft. In one embodiment, the spring lower portion is attached to the lower shaft and the spring upper portion slides within the spring slot. Thus, the only portion of the spring that can bend is the remaining crimped portion, and the bend tends to occur at the same point along this portion. In alternative embodiments, the spring may have a preexisting bend or crimp at the desired point of the apex. In another alternative embodiment, a crimp member may be attached to the shaft to distort the spring outwardly from the shaft at the desired apex. It is anticipated that the above, or other, means of creating the apex at a consistent, desired point may be employed in the present invention. Additionally, combinations of the various means of creating the apex at a consistent, desired point may be employed.

Although the spring may be a single piece, it is anticipated that the spring may also be constructed of two or more separate pieces cooperatively engaged to perform the described function. Other embodiments of the spring may also be incorporated into the suture device, such as using a spring that has a greater coefficient of elasticity in an area between the attachment point of the needle receiver and the attachment point of the spring lower portion to the lower shaft. This would result in the stiffening of the spring lower portion to more effectively withstand the pressure of pressing the needle through the tissue while in the second position, and would resist further bending and distortion of the spring, and ease insertion of the needle.

This deployment means provides the surgeon with an easy-to-use suturing device that deploys the needle quickly and efficiently. Furthermore, the needle is deployed and passed into the tissue under endoscopic vision to assure accurate placement in the tissue to receive the suture and also avoid other organs and tissue, such as the bowels, to prevent damage to them. Additionally, if the surgeon has not, or is unable to find the correct placement for the insertion of the needle, or if the device needs to be withdrawn without delivering the needle into the tissue, the needle is quickly retracted when force is removed from the spring.

Alternatively, the diameter of the shaft may be sized in order to fit through a cannula. Often, in endoscopic surgery, a trocar and cannula are used in order to create a passageway into the body cavity. The cannula may be made relatively airtight in order that gas can be pumped into the body cavity expanding the cavity. In this manner, the body cavity is made more accessible and visible to the surgeon. It is possible that in order to close the wound when a trocar and cannula have been used, the diameter of the shaft of the present invention may be sized so that it fits through the cannula. In this alternative embodiment, the shaft tip at the distal end of the suture device may be inserted through the cannula, the needles moved from a first position in the needle recess of the shaft to a second position extended from the shaft so that the surgeon may pull upwardly on the suture device inserting the needles into the tissue of the body wall at a location chosen by the surgeon. Once inserted, the needles are released from the needle receiver and the suture is pulled from the suture chamber in the shaft. The shaft can then be removed from the cannula (if present) and the body cavity, leaving the needles inserted through the tissue wall with the suture strung between them inside the tissue wall. Once the present invention and cannula are removed, the needles can then be drawn from the body wall to the outside of the body leaving suture line to pull close the tissue layers. The present invention works in similar fashion if the cannula is removed first, then the suture devise is inserted for deployment of the needles and suture.

BRIEF DESCRIPTION OF THE DRAWINGS

FIG. 1. is a partial perspective view of the present invention.

FIG. 2. is a partial perspective view of the present invention.

FIG. 3A. is a partial side view of the present invention.

FIG. 3B. is a partial side view of the present invention.

DETAILED DESCRIPTION OF THE PREFERRED EMBODIMENT

Figure 3C:
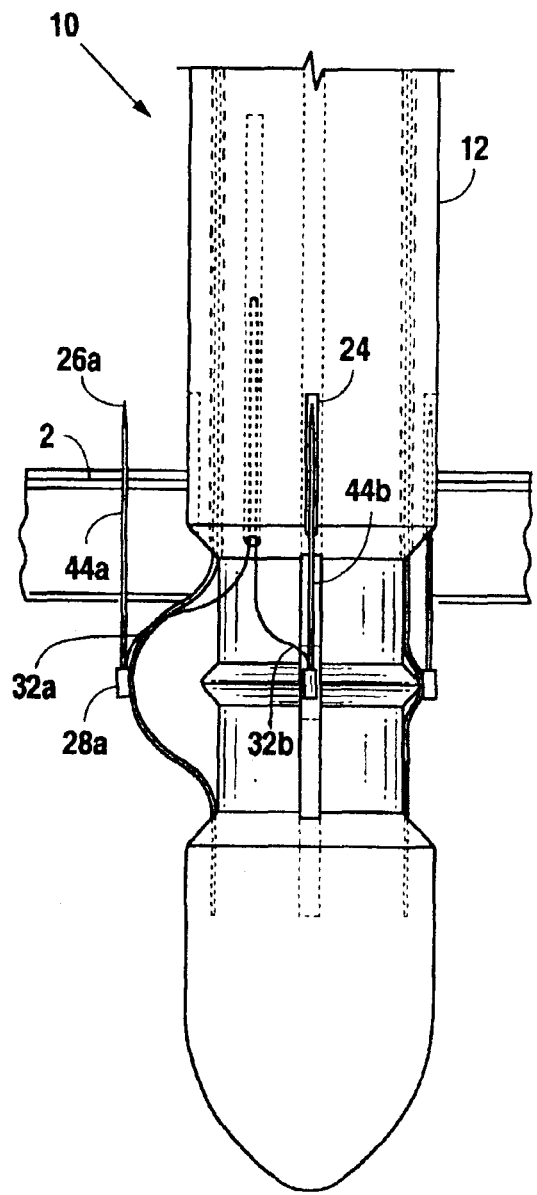
FIG. 3C. is a partial side view of the present invention.

Referring to the figures, FIG. 1. illustrates the distal end of the suture device. The distal end of the suture device includes a means for extending the needle (26). The proximal end of the suture device includes a means for activating the means for extending the needle (26). However, because it is anticipated that there will be a variety of embodiments of the means for activating, a specific embodiment is not shown. The means for activating, regardless of the embodiment, is required to place a force on the spring upper portion (41) such that the spring crimped portion (40) is bent outwardly from the shaft (10).

In the portion of the suture device shown, the shaft (10) is divided into three portions, the upper shaft (12), the inner shaft (14), and the lower shaft (16). The lower shaft (16) ends in a shaft tip (18) of the distal end of the suture device. In this embodiment of the suture device, the spring (38) is a straight spring that is attached by its spring lower portion (42) to the lower shaft (16). This attachment provides an anchor for the spring (38). The diameter of the lower shaft (16) is anticipated to be generally the same as that of the upper shaft (12). However, the inner shaft (14) is intended to be of a lesser diameter. This allows the spring lower portion (42) to extend into a lower shaft shoulder (34) and be anchored therein. The spring crimped portion (40) lays along the inner shaft (14) where it is exposed to the exterior environment. The spring upper portion (41) extends through an upper shaft shoulder (36) into a spring slot (20) in the upper shaft (12). The spring (38) is movably positioned inside the spring slot (20). The shaft (10) has a longitudinal axis (X—X) that extends between its proximal end and its distal end. The activation means is in operational engagement with the extension means, and thus the spring upper portion (41) through the spring slot (20).

Upon activation, force is placed upon the spring upper portion (41) parallel to the shaft longitudinal axis (X—X) from the proximal end to the distal end. This force on the spring upper portion (41) causes the spring upper portion (41) to slide distally within the spring slot (20). Because the spring lower portion (42) is attached to the lower shaft (16), the compression of the spring (38) causes the spring crimped portion (40) to bend outwardly from the inner shaft (14).

Because of the anchoring of the spring lower portion (42) in the lower shaft (16) and the positioning of the spring upper portion (41) within the spring slot (20), the only portion of the spring (38) that can deform upon a force being applied is the spring crimped portion (40) which is exposed to the external environment. Because the first position of the spring crimped portion (40) is adjacent to the inner shaft (14), the only direction the spring crimped portion (40) will deform is perpendicular to the shaft (10). Additionally, the apex of the bend of the spring crimped portion (40) will be at a predetermined point along the spring crimped portion (40). To further encourage the bend to occur at that predetermined point, the suture device may have a pre-made bend or crimp, or include a crimp member (30), each of which will cause a slight bend or weakness at the predetermined point of the spring crimped portion (40) which will encourage repeated bending at that same point. When the force is applied to the spring upper portion (41) and the spring upper portion (41) slides distally through the spring slot (20), the spring crimped portion (40) bends perpendicular to the shaft (10). Because of the elastic characteristics of the spring (38), the spring (38) will move from a first relaxed position when no force is applied, to a second tensioned position when force is applied.

It is anticipated that the spring will be made of metal or plastic, where metal, as used herein, is intended to include any metallic substance or compound containing a metallic substance, and plastic, as used herein, is intended to include any of the numerous organic, synthetic, or processed materials that are mostly thermoplastic or thermosetting polymers. The spring may also be made of one or multiple pieces that are cooperatively engaged in order to effect the same results as a single spring piece. It is intended that the spring (38), regardless of its material or the number of pieces, have the inherent characteristic that causes it to deform upon having a force applied to it, but elastically return to its original shape after the force is removed.

The goal of the suture device is to have the needle (26) extend parallel to the longitudinal axis (X—X) of the shaft (10). Also due to the characteristics of the spring (38), when the spring crimped portion (40) moves from the first position to the second position, the apex of its bend will move perpendicularly to the longitudinal axis (X—X). A needle receiver (28) is attached at the apex of the bend in the spring crimped portion (40). Therefore, because the apex of the bend in the spring crimped portion (40) moves perpendicular to the longitudinal axis (X—X) of the shaft (10), the needle receiver (28) will move perpendicularly as well.

A needle (26) is removably attached at its second end (26B) to the needle receiver (28). The needle's second end (26B) is further attached to a suture (32) at a suture first end (32A). The suture (32) extends out of the needle receiver (28) and a suture excess portion (32C) may be removably inserted into a suture chamber (22) in the shaft (10). If multiple needles (44A and 44B, as shown in FIG. 2) are incorporated in the suture device, then the suture first end (32A) is attached to the first needle (44A, as shown in FIG. 2) and the suture second end (32B) is attached to the second needle (44B, as shown in FIG. 2) with the suture excess (32C) removably inserted in the suture chamber (22).

In order to more easily extend the shaft tip (18) and lower shaft (16) (the distal end of the suture device) through the tissue layer (2, as shown in FIGS. 3A, 3B, 3C, and 3D), the upper shaft (12) may include a needle recess (24) that accepts the needle (26) so that the needle (26) is held in the first position inside the diameter of the shaft (10). In this manner, the needle (26) is less likely to snag or catch on the tissue layer (2, as shown in FIGS. 3A, 3B, 3C, and 3D) when the shaft (10) is inserted through the tissue layer (2, as shown in FIGS. 3A, 3B, 3C, and 3D). When the extension means is moved from the first position to the second position, the needle (26) is extended along with the needle receiver (28) to a position outside the outer diameter of the shaft (10). This exposes the needle first end (26A) for engagement with the tissue layer (2, as shown in FIGS. 3A, 3B, 3C, and 3D).

FIG. 2. shows the suture device with a first needle (44A) in the second tensioned position and a second needle (44B) in the first relaxed position. As shown in this figure, multiple needles (26) are shown as first needle (44A) and second needle (44B). The second needle (44B) remains in the first position within the needle recess (24). Conversely, the means for exerting force on the first spring (38A) has been activated causing the first spring (38A), first needle receiver (28A), and first needle (44A) to move to the second position with the first needle (44A) outside of the needle recess (24). Because it is anticipated that a surgeon may wish to use a first needle (44A) and a second needle (44B) connected by a common suture (32), that provision may be accommodated in an embodiment of the suture device.

It is further anticipated that there may be other multiple pairings of needles (26). In this manner, a paired first needle (44A) and second needle (44B) would be joined by a common suture (32) where the surgeon would be able to insert the distal portion of the shaft (10) through the tissue layer (2, as shown in FIGS. 3A, 3B, 3C, and 3D) and into the body cavity (not shown), move the suture device so as to choose an insertion point in the tissue layer (2, as shown in FIGS. 3A, 3B, 3C, and 3D) for the first needle (44A), then the means for activating the means for extending is engaged and the first needle (44A) is moved from the first position to the second position, and finally the first needle (44A) is inserted into the tissue layer (2, as shown in FIGS. 3A, 3B, 3C, and 3D). The first needle (44A) can then be disengaged from the first needle receiver (28A) and the process is repeated for the second needle (44B). Once both the first needle (44A) and the second needle (44B) are engaged in the tissue layer (2, as shown in FIGS. 3A, 3B, 3C, and 3D), the suture device can be removed leaving the first needle (44A) and the second needle (44B) partially exposed on the external surface of the tissue layer (2, as shown in FIGS. 3A, 3B, 3C, and 3D). The surgeon can then pull out the first needle (44A) and the second needle (44B) and draw together with the suture (32) the wound in the tissue layer (2, as shown in FIGS. 3A, 3B, 3C, and 3D).

FIGS. 3A, 3B, 3C, and 3D illustrate the use of the present invention. In FIG. 3A, the distal portion of the shaft (10) has been inserted through a wound or opening in the tissue layer (2). If a cannula (not shown) was being used, then the diameter of the shaft (10) would be sized to fit within the aperture of the cannula (not shown). However, other than size limitations, it is anticipated that the present invention could be used with or without a cannula. In this first figure, the needles (26) are in the first relaxed position as are the springs (38). As previously described, the relatively larger diameters of the lower shaft (16) and the upper shaft (12), as well as the needle recesses (24) help resist unwanted catching or snagging of the tissue layer (2) by any portion of the suture device.

In FIG. 3B, the first needle (44A) has been moved to the second position. A comparison of FIGS. 3A and 3B illustrates how the first spring crimped portion (40A) bends at the crimped member (30) and the apex of the bend stays relatively perpendicular at the second position shown in FIG. 3B as to the first position shown in FIG. 3A. As a result, the first needle (44A) is held generally perpendicular to the longitudinal axis (X—X) of the shaft (10). This helps the surgeon because the first end (26A) of the first needle (44A) will enter the tissue layer (2) at a generally known point as opposed to if the first needle (44A) was held at an angle or was curved, in which case, it is less intuitive for the surgeon to be able to pick the insertion point of the first needle (44A). A second benefit is that when the first needle (44A) exits the tissue layer (2) on the external side, it will be at a known position relative to the insertion point.

Once the surgeon has inserted the suture device into the body cavity as shown in FIG. 3A, the surgeon then chooses a point for insertion of the first needle (44A) and moves the suture device relative to the tissue layer (2) in order to align the first needle's (44A) first end (26A) with that chosen insertion point. The surgeon then, using the means for activation, exerts pressure on the first spring (38A) such that the first spring upper portion (41A) slides through the spring slot (20) and causes the first spring crimped portion (40A) to bend outwardly with the first needle receiver (28A).

FIG. 3C. illustrates the insertion of the first needle (44A) into the tissue layer (2). By pulling on the suture device, the surgeon causes the insertion of the needle first end (26A) into and through the tissue layer (2). The first needle (44A)

is supported in urging it through the tissue layer (2) by the first needle receiver (28A). During this time, the second needle (44B) remains in the first position protected from engaging the tissue layer (2) by being held in the first position within the needle recess (24).

Figure 3D:
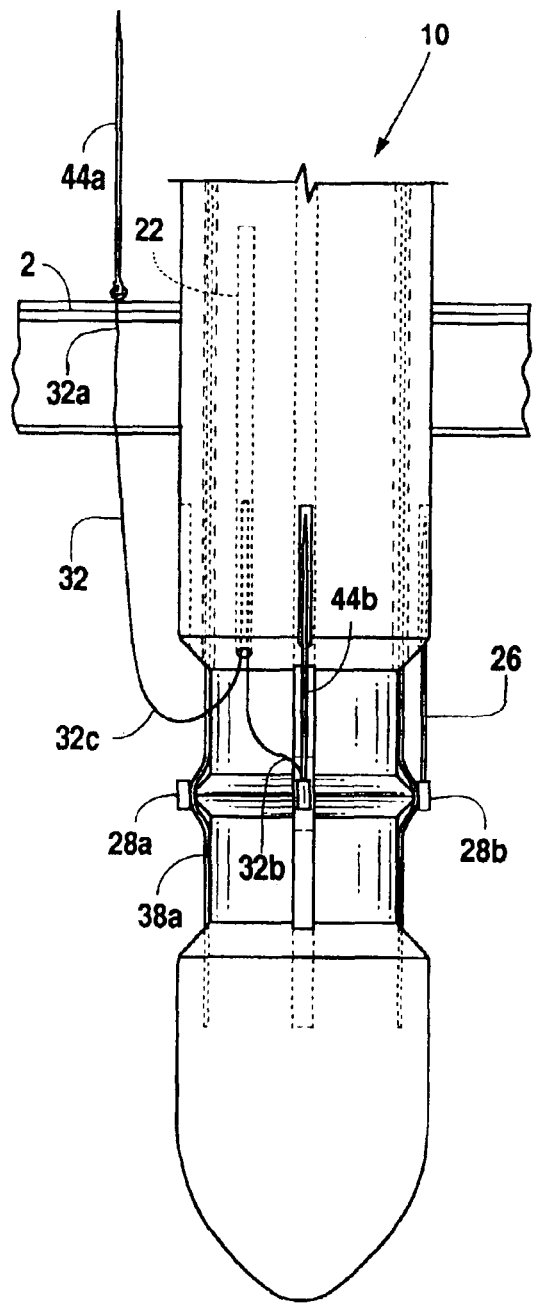
FIG. 3D. is a partial side view of the present invention.

FIG. 3D. illustrates the conclusion of the insertion of the first needle (44A). Once the first needle (44A) is inserted through the tissue layer (2), it may be grasped by the operator (surgeon) with a conventional tool and pulled from first needle receiver (28A) and the wound. Or, the suture device can be urged back into the body cavity dislodging the first needle (44A) from the first needle receiver (28A) leaving the first needle (44A) inserted through the tissue layer. In either case, the suture first end (32A) remains attached to the first needle (44A) passing back through the fascia to the suture second end (32B) that is attached to the second needle (44B). As the needles (44A and 44B) are removed from the first and second needle receivers (28A and 28B), the suture excess (32C) is pulled from the suture chamber (22). After the first needle (44A) is dislodged from the first needle receiver (28A), the means for activation can be disengaged and the inherent elastic characteristics of the first spring (38A) cause it to move from the second tensioned position to the first relaxed position. Thus, the extension means will, if no force is exerted by the activation means on it, move to and remain at rest in the first relaxed position.

Once the first needle (44A) has been dislodged from the first needle receiver (28A), the suture device can be repositioned and the process repeated for the second needle (44B). The first needle (44A) and the second needle (44B) can be drawn from the tissue layer (2) and the wound in the tissue layer (2) closed by the excess suture (32C). The surgeon then ties off the suture (32) to hold the tissue layer (2) together. If multiple pairs of needles (26) are used, then the process can be repeated for the requisite number of times such that multiple sutures (32) are left with multiple needles (26) and sutures (32) to close the wound.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A suture device for suturing puncture wounds in a body cavity wall comprising:
   a shaft having a spring slot;
   a spring having an upper portion, a crimped portion, and a lower portion, said upper portion moveably positioned in said spring slot;
   said spring lower portion attached to said shaft,
   said spring crimped portion having a first relaxed position relatively near said shaft, and a second tensioned position relatively extended from said shaft said spring capable of moving between the first relaxed position and the second tensioned position; and;
   a needle receiver attached to said spring crimped portion.

2. The apparatus of claim 1, further comprising:
   a crimp member attached to said shaft between said shaft and said spring crimped portion such that said crimp member causes a bend in said spring when said spring is in said first relaxed position.

3. The apparatus of claim 1, further comprising:
   a first needle removably attached to said needle receiver.

4. The apparatus of claim 3, further comprising:
   a suture attached to said first needle.

5. The apparatus of claim 3, further comprising:
   a suture having a first end attached to said first needle, and an excess suture;
   a suture chamber in said shaft; and
   said excess suture removably contained in said suture chamber.

6. The apparatus of claim 5, further comprising:
   a suture second end attached to a second needle.

7. The apparatus of claim 3, wherein said needle is held substantially parallel to said shaft both when said spring crimped portion is in said first relaxed position and when said spring crimped portion is in said second tensioned position.

8. The apparatus of claim 1, wherein said spring returns to said first relaxed position if no force is exerted on said spring upper portion.

9. The apparatus of claim 8, wherein said spring is made of metal or plastic.

10. The apparatus of claim 1, wherein said shaft is cylindrical and has a diameter that is sized to fit in an aperture of a cannula.

11. The apparatus of claim 1, wherein said shaft has a diameter that is sized to fit through a defect caused by a cannula.

12. The apparatus of claim 1, wherein said spring has a greater coefficient of elasticity in an area between an attachment point of said needle receiver and an attachment point of said spring lower portion to said lower shaft.

13. The apparatus of claim 1, wherein said spring is crimped at a desired point in the spring crimped portion for said bend to occur in said second tensioned position while said spring is in said first relaxed position.

14. A suture device for suturing puncture wounds in a body cavity wall comprising:
   a shaft having a spring slot;
   a spring having an upper portion, a crimped portion, and a lower portion, said upper portion moveably positioned in said spring slot;
   said spring lower portion attached to said shaft;
   said spring crimped portion having a first relaxed position relatively near said shaft, and a second tensioned position relatively extended from said shaft;
   a needle receiver attached to said spring crimped portion; and
   a crimp member attached to said shaft between said shaft and said spring crimped portion such that said crimp member causes a bend in said spring when said spring is in said first relaxed position.

15. The apparatus of claim 14, wherein said spring returns to said first relaxed position if no force is exerted on said spring upper portion.

16. The apparatus of claim 14, further comprising:
   a suture having a first end attached to a first needle, said first needle removably attached to said needle receiver wherein said needle is held substantially parallel to said shaft both when said spring crimped portion is in said first relaxed position and when said spring crimped portion is in said second tensioned position.

17. The apparatus of claim 14, further comprising:
   a suture chamber in said shaft; and
   a portion of said suture removably contained in said suture chamber.

18. The apparatus of claim 14, further comprising:
a suture second end attached to a second needle.

19. The apparatus of claim 14, wherein said spring is made of metal or plastic.

20. The apparatus of claim 14, wherein said shaft is cylindrical and has a diameter that is sized to fit in an aperture of a cannula.

21. The apparatus of claim 14, wherein said shaft has a diameter that is sized to fit through a defect caused by a cannula.

22. The apparatus of claim 14, wherein said spring has a greater coefficient of elasticity in an area between an attachment point of said needle receiver and an attachment point of said spring lower portion to said lower shaft.

23. The apparatus of claim 14, wherein said spring is crimped at a desired point in the spring crimped portion for said bend to occur in said second tensioned position while said spring is in said first relaxed position.

24. A suture device for suturing puncture wounds in a body cavity wall comprising:

a shaft having a spring slot;

a spring having an upper portion, a crimped portion, and a lower portion, said upper portion moveably positioned in said spring slot;

said spring lower portion attached to said shaft;

said spring crimped portion having a first relaxed position relatively near said shaft, and a second tensioned position relatively extended from said shaft;

a needle receiver attached to said spring crimped portion;

a crimp member attached to said shaft between said shaft and said spring crimped portion such that said crimp member causes a bend in said spring when said spring is in said first relaxed position; and a suture having a first end attached to a first needle, said first needle removably attached to said needle receiver wherein said needle is held substantially parallel to said shaft both when said spring crimped portion is in said first relaxed position and when said spring crimped portion is in said second tensioned position.

25. The apparatus of claim 24, wherein said shaft has a diameter that is sized to fit through a defect caused by a cannula.

26. The apparatus of claim 24, wherein said spring is comprised of more than one piece.

27. The apparatus of claim 24, wherein said spring has a greater coefficient of elasticity in an area between an attachment point of said needle receiver and an attachment point of said spring lower portion to said lower shaft.

28. The apparatus of claim 24, wherein said spring is crimped at a desired point in the spring crimped portion for said bend to occur in said second tensioned position while said spring is in said first relaxed position.

29. A suture device for suturing punctures wounds in a body cavity wall comprising:

a needle;

a means for extending said needle, said needle having a first end and a second end, where said needle is removably attached to said means for extending, wherein said means for extending moves said needle from a first position to a second position, and wherein a line running from said needle first end to said needle second end when said needle is in said first position is substantially parallel to a line running from said needle first end to said needle second end when said needle is in said second position;

a shaft having a proximal end and a distal end with a longitudinal axis extending between said proximal end and said distal end, said means for extending attached to said distal end of said shaft;

a needle recess in the surface of said shaft, wherein said first position is substantially within said needle recess and said second position is substantially outside of said needle recess; and a spring having an upper portion, a crimped portion, and a lower portion; said upper portion moveably attached to said shaft, said spring lower portion attached to said shaft, said needle removably attached to said crimped portion; and wherein said spring holds said needle in said first position if no force is exerted on said spring upper portion.

30. The apparatus of claim 29, further comprising:

a suture chamber in said shaft; and a suture having a first end attached to said needle, and the majority of the remainder of said suture removably positioned inside said suture chamber.

31. The apparatus of claim 29, wherein said shaft is cylindrical and has a diameter that is sized to fit in an aperture of a cannula.

32. The apparatus of claim 29, wherein said shaft has a diameter that is sized to fit through a defect caused by a cannula.

33. The apparatus of claim 29, wherein said spring is comprised of more than one piece.

34. The apparatus of claim 29, wherein said spring has a greater coefficient of elasticity in an area between an attachment point of said needle receiver and an attachment point of said spring lower portion to said lower shaft.

35. The apparatus of claim 29, wherein said spring is crimped at a desired point in the spring crimped portion for said bend to occur in said second tensioned position while said spring is in said first relaxed position.

* * * * *